United States Patent [19]

Greenwald

[11] 4,006,150

[45] Feb. 1, 1977

[54] ALKYLSULFONYL METHYL-SUBSTITUTED PYRIDINE N-OXIDES

[75] Inventor: Richard B. Greenwald, Lexington, Mass.

[73] Assignee: Polaroid Corporation, Cambridge, Mass.

[22] Filed: Mar. 31, 1976

[21] Appl. No.: 672,291

[52] U.S. Cl. .............. 260/294.8 F; 260/326.12 R; 260/343.2 R; 260/438.5 R; 96/29 D
[51] Int. Cl.[2] .................................... C07D 213/34
[58] Field of Search ............. 260/294.8 F; 96/29 D

[56] References Cited

UNITED STATES PATENTS 3,444,175   5/1969   Shen et al. .................. 260/294.8 F

OTHER PUBLICATIONS

Shen et al., Chem. Abstracts, vol. 71(17), 81,357N, Oct. 27, 1969.

*Primary Examiner*—Alan L. Rotman
*Attorney, Agent, or Firm*—Sybil A. Campbell

[57] ABSTRACT

This invention is concerned with pyridine N-oxides substituted in the ortho and/or para position with an alkylsulfonylmethyl group which find utility in photography for effecting an increase in photographic speed.

8 Claims, No Drawings

ALKYLSULFONYL METHYL-SUBSTITUTED PYRIDINE N-OXIDES

BACKGROUND OF THE INVENTION

1. Field of the Invention

This invention relates to novel compounds useful as speed increasers in dye developer diffusion transfer photographic processes and to color diffusion transfer processes, products and compositions employing the same.

2. Description of the Prior Art

U.S. Pat. No. 2,983,606 issued May 9, 1961, to Howard G. Rogers discloses photographic processes employing dye developers to form diffusion transfer color images. U.S. Pat. No. 3,345,163 issued Oct. 3, 1967 to Edwin H. Land and Howard G. Rogers discloses the use of such dye developers in integral multilayer negatives to give multicolor transfer images.

The present invention is concerned with dye developer diffusion transfer processes conducted in the presence of N-oxides of certain N-heterocyclylalkyl sulfones and with a novel class of such compounds useful therein.

SUMMARY OF THE INVENTION

It is one object of the present invention to provide novel N-oxides of alkylsulfonylmethylpyridines useful in dye developer diffusion transfer processes.

It is another object of the present invention to provide diffusion transfer color processes employing dye developers wherein an increase in photographic speed is obtained by performing the process in the presence of an ortho-and/or para-alkylsulfonylmethylpyridine N-oxide.

It is yet another object of the present invention to provide photographic products and compositions useful in such processes.

Other objects of this invention will in part be obvious and will in part appear hereinafter.

The invention accordingly comprises the processes involving the several steps and the relation and order of one or more of such steps with respect to each of the others, and the products and compositions possessing the features, properties and the relation of elements, which are exemplified in the following detailed disclosure, and the scope of the application which will be indicated in the claims.

For a fuller understanding of the nature and objects of the invention, reference should be had to the following detailed description.

DESCRIPTION OF THE PREFERRED EMBODIMENTS

According to the present invention it has been found that certain alkylsulfonylmethylpyridine N-oxides when employed in photographic dye developer diffusion transfer processes provide an increase in photographic speed, particularly an increase in the red speed at cooler temperatures. The pyridine N-oxides (pyridine 1-oxides) found especially useful for this purpose are those substituted in the ortho and/or para position, i.e., in the 2- and/or 4-position with an alkylsulfonylmethyl group. Compounds of this type found particularly useful for effecting an increase in photographic speed in the aforementioned processes are those represented in the following formula

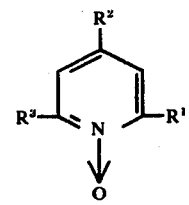

wherein $R^1$ is hydrogen or $-CH_2SO_2R$ wherein R is lower alkyl having 1 to 4 carbon atoms; $R^2$ is hydrogen, lower alkyl having 1 to 4 carbon atoms or said $-CH_2SO_2R$ and $R^3$ is hydrogen or lower alkyl having 1 to 4 carbon atoms, at least one of said $R^1$ and $R^2$ being $-CH_2SO_2R$.

Specific examples of alkylsulfonylmethylpyridine N-oxides within the scope of the present invention are as follows:

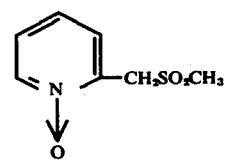

(1)

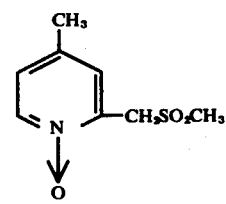

(2)

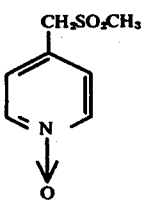

(3)

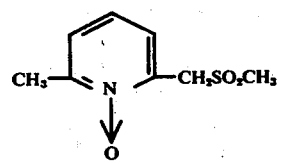

(4)

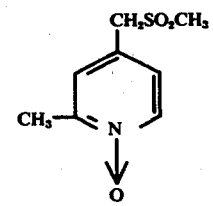

(5)

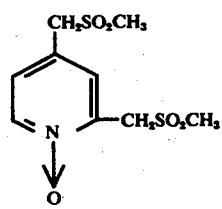

(6)

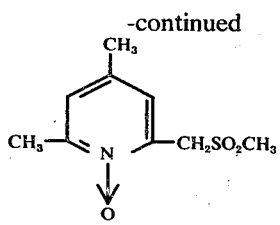
(7)

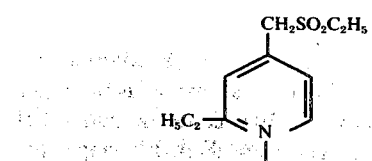
(8)

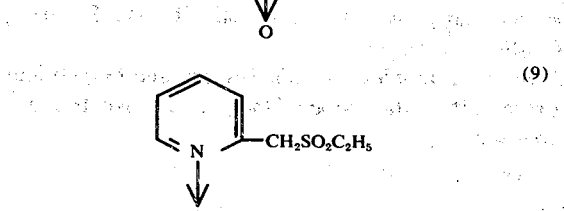
(9)

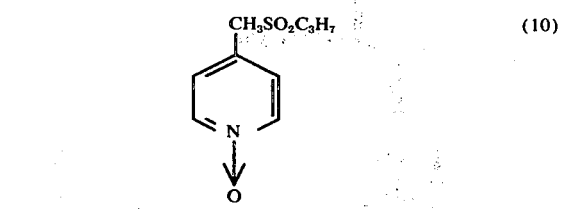
(10)

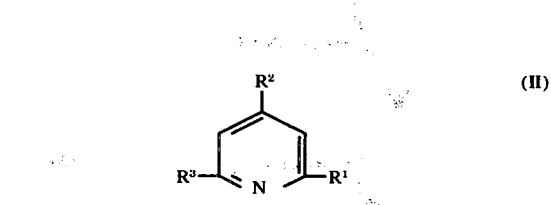
(II)

The compounds of formula (I) which comprise the novel compounds of the present invention may be synthesized, for example, by treating a pyridine of the formula wherein $R^1$, $R^2$ and $R^3$ have the same meaning given above with an oxidizing agent, such as, peracetic said, perbenzoic acid or m-chloroperbenzoic acid to yield the corresponding N-oxide. The alkylsulfonylmethyl-substituted compounds of formula II may be prepared as described in U.S. Pat. No. 3,444, 175, for example, by reacting an alkali metal sulfinate, $M^+SO_2^-R$ wherein R has the same meaning given above, and a pyridine appropriately substituted with —$CH_2X$ group (s) wherein X represents halo, such as, chloro.

Also, the subject compounds may be prepared by the oxidation of alkylthiomethyl-substituted pyridines, i.e., pyridines identical to those of formula II except that —$CH_2SR$ is substituted for —$CH_2SO_2R$, by treating with potassium permanganate to convert the —$CH_2SR$ to —$CH_2SO_2R$ followed by treatment with, e.g., peracetic acid to yield the N-oxide. The alkylthiomethyl-substituted compounds may be prepared from pyridines appropriately substituted with —$CH_2X$ group(s) by reaction with a mercaptide, $RS^-M^+$, wherein M is, eg., an alkali metal and R has the same meaning given above. The alkylthiomethyl-substituted compounds also may be prepared from pyridines substituted with —$CH_2SH$ group(s) by reaction with an alkali metal phenoxide or alkoxide, e.g., RONa wherein R has the same meaning given above.

In addition to the above, it will be appreciated by those skilled in the art that other methods have been reported for preparing alkylthiomethyl-substituted pyridines and for oxidizing the alkylthiomethyl group(s) to the corresponding alkylsulfonylmethyl group(s) and for oxidizing pyridines to the corresponding N-oxides, ie., 1-oxides. Also, it will be appreciated by those skilled in the art that the N-oxide portion of the subject compounds alternately may be represented by the formula

The following examples illustrate the preparation of compounds within the scope of this invention and are given for purposes of illustration only.

EXAMPLE 1

Preparation of 2-(methylsulfonylmethyl)-pyridine 1-oxide:

A solution of 2-picolylchloride hydrochloride (90 g., 0.55 mole) was dissolved in 1 liter ethanol and treated with potassium hydroxide pellets (30.9 g., 0.55 mole). The mildly exothermic neutralization was followed by the addition in one portion of sodium methane sulfinate hemi-hydrate (61 g., 0.55 mole). After heating the pale peach-colored reaction mixture at reflux for 2 hours, during which time a deep persimmon color developed, the reaction mixture was allowed to cool to room temperature overnight. Some long needles were observed in addition to granular white solid; thus, the reaction mixture was warmed briefly, filtered by suction while warm, and the alcohol stripped on a rotary evaporator to give a yellow crystalline solid residue. Trituration with 200 ml. cold water gave 2-(methylsulfonylmethyl)-pryidine (71 g., 75 % by weight) as a pale yellow solid, melting range 123°—125° C.

Meta-chloroperbenzoic acid, 85% solution, 1.27 g., 6 mmoles) was added to 2-(methylsulfonylmethyl)-pyridine .08 g., 6 mmoles) in 10 mls. of ethylene chloride. The resulting solution was allowed to stand at room temperature overnight and then was chilled and filtered. The filtrate was evaporated and cyrstallization of the oily residue was induced by scratching. Recrystallization from toluene and isopropanol gave 0.6 g. of the title compound as white needles (melting range 153-155° C.). Analysis for $C_7H_9NO_3S$:

|  | C | H | N |
|---|---|---|---|
| Calculated | 44.96 | 4.85 | 7.49 |
| Found | 44.57 | 4.77 | 7.59 |

EXAMPLE 2

Preparation of 2-(methylsulfonylmethyl)-6-methyl-pyridine 1-oxide:

A solution of sodium hydroxide (5.7 g.,) dissolved in 37 mls. of water was diluted with 40 mls. of ethanol, and the resulting solution was saturated with methylmercaptan.

6-methyl-2-picolylchloride hydrochloride (25 g.) was dissolved in 25 mls. of water. The picolylchloride solution was diluted with 100 mls. of ethanol, neutralized with a solution of 5.7 g. of sodium hydroxide in 37 mls. of water and then added to the methylmercaptan solution. The reaction mixture was refluxed for 3 hours and allowed to stand overnight. The ethanol was removed by evaporation and then the organic phase was separated from the aqueous phase. The aqueous phase was extracted two times with 200 mls. of ether and the ether was extracted with 50% aqueous sodium chloride, dried, evaporated and the residue distilled to give 16 g. of 2-(methylthiomethyl)-6-methylpyridine as a light yellow liquid, boiling point approx. 65° C. at 4 mm.

The methylthiomethylpyridine prepared above (1.5 g., 0.01 M) was dissolved in 10 mls. of acetic acid. The solution was placed in a water bath and 40% peracetic acid (0.03 M) was added. The reaction mixture was stirred 1 hour at room temperature and then heated on a steam bath for one half hour. The excess peroxide was decomposed with sodium bisulfite and the solution was evaporated and the residue extracted with isopropanol to give 1 g. of the title compound, melting range 131°–135° C. Analysis for $C_8H_{11}NSO_3$:

|  | C | H | N |
|---|---|---|---|
| Calculated | 47.65 | 5.5 | 7.00 |
| Found | 47.93 | 5.96 | 6.87 |

EXAMPLE 3

Preparation of 4-(methylsulfonylmethyl)-pyridine 1-oxide:

4-(methylthiomethyl)-pyridine (1.4 g.) was dissolved in 10 mls. of glacial acetic acid. The solution was cooled in a water bath and 6 g. of 40% peracetic acid was added. The reaction solution was stirred overnight and then heated on a steam bath for one hour. The excess peracetic acid was decomposed with sodium bisulfite and the solution was evaporated. The residue was recrystallized from methanol to give 1.9 g. of the title compound, melting range 194°–198° C. Analysis for $C_7H_9NO_3S$

|  | C | H | N |
|---|---|---|---|
| Calculated | 44.96 | 4.85 | 7.49 |
| Found | 45.03 | 4.89 | 7.42 |

As noted previously, the present invention is concerned with pyridine N-oxides substituted in the ortho and/or para position with an alkylsulfonylmethyl group, i.e., alkylSO$_2$CH$_2$— and also with the use of such compounds in dye developer diffusion transfer processes. In a preferred embodiment, these compounds are used in dye developer diffusion transfer processes wherein the desired color transfer image is a multicolor image obtained by processing an exposed multicolor photosensitive silver halide element with a processing composition distributed between two sheet-like elements, one of said elements including an image-receiving layer. The processing composition is so applied and confined within and between the two sheetlike elements as not to contact or wet outer surfaces of the superposed elements, thus providing a film unit or film packet whose external surfaces are dry. The processing composition, which may be viscous or nonviscous, preferably is distributed in viscous form a single-use rupturable container; such pressure rupturable processing containers are frequently referred to as "pods".

Multicolor diffusion transfer images may be obtained using dye developers by several techniques. A particularly useful technique employs an integral multilayer photosensitive element, such as is disclosed in the aforementioned U.S. Pat. No. 2,983,606, and particularly with reference to FIG. 9 thereof, and in aforementioned U.S. Patent No. 3,345,163, wherein at least two selectively sensitized photosensitive strata, superposed on a common support, are processed, simultaneously and without separation, with a single (common) image-receiving layer. A suitable arrangement of this type for obtaining multicolor images utilizing subtractive color principles comprises a support carrying a red-sensitive silver halide emulsion stratum, a greensensitive silver halide emulsion stratum and a blue-sensitive silver halide emulsion stratum, said emulsions having associated therewith, respectively, a cyan dye developer, a magenta dye developer and a yellow dye developer. The dye developer may be positioned in the silver halide emulsion stratum, for example in the form of particles, or it may be disposed in a stratum behind the appropriate silver halide emulsion stratum with respect to the exposing light. Each set of silver halide emulsion and associated dye developer strata may be separated from other sets by suitable interlayers, for example, by a layer or stratum of gelatin, polyvinyl alcohol, or other polymeric materials known in the art. In certain instances, it may be desirable to incorporate a yellow filter in front of the green-sensitive emulsion to avoid improper exposure of said emulsion, by blue light, and such a yellow filter may be incorporated in the appropriately positioned interlayer. However, such a separate yellow filter may be omitted where a yellow dye developer of the appropriate spectral characteristics is present in a quantity and state capable of functioning as the requisite yellow filter. Procedures and suitable components for preparing such integral multicolor photosensitive elements are described in numerous patents and are well known in the art.

Following photoexposure, the photosensitive element is processed by application of a processing composition, for example, by immersion, coating, spraying, flowing, etc., in the dark. The exposed photosensitive element may be superposed prior to, during, or after application of the processing composition on a sheet-like element which may include an image-receiving layer. In one commercial embodiment, the processing composition is applied to the photosensitive element in a substantially uniform layer as the photosensitive element is brought into superposed relationship with the image-receiving layer. The liquid processing composition permeates the layers of the photosensitive element to initiate and effect development of the latent images contained therein. The dye developers are immobilized or precipitated imagewise in developed areas as a consequence of and in proportion to the silver halide development. This immobilization is, at least in part, due to a change in the solubility characteristics of the dye developers upon oxidation and especially as regards its solubility in alkaline solution. In undeveloped and partially developed areas of the silver halide emulsion layers, the respective unoxidized (unreacted) dye developers are diffusible. Development thus provides an imagewise distribution of unoxidized dye developer, diffusible in the alkaline processing composition, as a function of the point-to-point degree of exposure of a silver halide emulsion layer. At least part of each of these imagewise distributions of unoxidized dye developer is transferred, by imbibition, to a superposed image-receiving layer, said transfer substantially excluding oxidized dye developer. The image-receiving layer receives a depthwise diffusion, from each developed silver halide emulsion, of unoxidized dye developer without appreciably disturbing the imagewise distribution thereof to provide a reversed or positive color image of each developed silver image. The image-receiving layer may contain a mordant and/or other agent to immobilize the dye developer transferred thereto. If the color of a transferred dye developer is affected by changes in the pH of the image-receiving layer, this pH may be adjusted in accordance with well-known techniques to provide a pH affording the desired color. In the preferred embodiments of said U.S. Pat. No. 2,983,606 and in certain commercial applications thereof, the desired positive multicolor image is viewed by separating the image-receiving layer from the photosensitive element at the end of a suitable imbibition period.

In a more recent commercial application of the dye developer process, the image-receiving layer is not separated from its superposed relationship with the photosensitive layers subsequent to transfer image formation. Instead, the color image in the image-receiving layer is viewed through a transparent support. The aforementioned U.S. Pat. No. 2,983,606 discloses such an embodiment, the processing composition including a white pigment, such as titanium dioxide, in a quantity effective to mask or "hide" from view the developed silver halide emulsions now positioned behind the image-receiving layer when the image-receiving layer is viewed through the transparent support.

U.S. Pat. Nos. 3,415,644, 3,415,645 and 3,415,646 all issued December 10, 1968 in the name of Edwin H. Land disclose and claim photographic products and processes wherein a photosensitive element and an image-receiving element are maintained in fixed, superposed relationship prior to exposure, and this relationship is maintained as a laminate after processing and transfer image formation. The multicolor transfer image is viewed through a transparent (support) sheet against a reflecting, i.e., white, background. In a particularly useful embodiment, photoexposure is made through said transparent support and the layers carried thereon, including the image-receiving layer, and application of the processing composition provides a layer of light-reflecting material to provide a white background. The light-reflecting material (referred to in said patent as an "opacifying agent") is preferably titanium dioxide but a number of other materials have been disclosed as useful. In addition to providing a masking layer so the transfer image may be viewed without interference by the images in the developed silver halide emulsions, the light-reflecting material also performs an opacifying function by reflecting ambient light passing through the image-receiving layer and its transparent support when the photoexposed film unit is removed from the camera before transfer image formation is completed, thereby acting to protect the photoexposed silver halide emulsions from post-exposure fogging by such light.

U.S. Pat. No. 3,647,437 issued Mar. 7, 1972 to Edwin H. Land is concerned with improvements in the above-mentioned processes, and discloses the provision of a light-absorbing material, sometimes referred to as an optical filter agent, to permit such processes to be performed outside of the camera in which photoexposure is effected and to be so performed under much more intense ambient light conditions. The light-absorbing material or optical filter agent, preferably a dye, is so positioned in the film unit and/or constituted as not to interfere with photoexposure (by absorbing light during photoexposure) but so positioned between the photoexposed silver halide emulsions and the transparent support during processing after photoexposure as to absorb light which otherwise might fog the photoexposed emulsions. Furthermore, the light-absorbing material is so constituted and/or positioned after processing as not to interfere with viewing the desired image in its proper colors shortly after said image has been formed. In the preferred embodiments, the optical filter agent is a dye and is initially contained in the processing composition together with a light-reflecting material, e.g., titanium dioxide. The concentration of this light-absorbing dye is selected to provide the light transmission opacity required to perform the particular process under the selected light conditions, and a plurality of such dyes selected to together provide absorption over the visible spectrum is utilized in multicolor embodiments.

In a particularly useful embodiment, the light-absorbing dye is highly colored at the pH of the processing composition, e.g., 13–14, but is substantially non-absorbing of visible light at a lower pH, e.g., less than 10–12. This pH reduction may be effected by an acid-reacting reagent appropriately positioned in the film unit, e.g., in a layer between the transparent support and the image-receiving layer. Suitable acid-reacting reagents, preferably polymeric acids, are disclosed in the aforementioned U.S. Pat. Nos. 3,415,644 and 3,647,437 to which reference may be made for more specific information.

Suitable materials for use as the image-receiving layer are disclosed in the aforementioned patents. Preferred image-receiving layers comprise polyvinyl alcohol or gelatin containing a dye mordant such as poly-4-vinylpyridine, as disclosed in U.S. Pat. No. 3,148,061, issued September 8, 1964.

As disclosed in the previously cited patents, the liquid processing composition referred to for effecting multicolor diffusion transfer processes comprises at least an aqueous solution of an alkaline material, for example, sodium hydroxide, potassium hydroxide, and the like, and preferably possesses a pH in excess of 12, and most preferably includes a viscosity-increasing compound constituting a film-forming material of the type which, when the composition is spread and dried, forms a relatively firm and relatively stable film. Preferred film-forming materials comprised high molecular weight polymers such as polymeric, water-soluble ether, for example, a hydroxyethyl cellulose or sodium carboxymethyl cellulose, which are substantially inert in alkaline solution. Other film-forming materials or thickening agents whose ability to increase viscosity is unimpaired if left in alkaline solution for extended periods of time also may be used. The film-forming material is preferably contained in the processing composition in such suitable quantities as to impart to the composition a viscosity appropriate for the particular method of application to be used, such viscosity being in excess of 100 cps. at a temperature of approximately 24° C. and preferably in the order of 100,000 cps. to 200,000 cps. at that temperature.

Dye developers are well known in the art and are compounds which contain both a silver halide developing function and the chromophoric system of a dye. By "a silver halide developing function" is meant a grouping adapted to develop exposed silver halide. The dye developer as incorporated in the photosensitive element may have a "latent" silver halide developing function, i.e., the dye developer may contain a moiety which is a precursor of the silver halide developing function or moiety, the active functional group being formed in situ following application of the processing composition, e.g., by alkaline hydrolysis of an esterified hydroquinonyl group. A preferred silver halide developing function is a hydroquinonyl group. Other particularly useful developing functions include ortho-dihydroxyphenyl and ortho-and para-amino substituted hydroxyphenyl groups. In general, the developing function includes a benzenoid silver halide developing function, that is, an aromatic silver halide developing group which forms quinonoid or quinone substances when oxidized. The dye developers usually are selected for their ability to provide colors useful in carrying out subtractive color photography, e.g., cyan, magenta and yellow. Other colors, of course, may be provided to meet the needs of a particular system.

For convenience, the disclosures of the abovementioned U.S. Pat. Nos. 2,983,606, 3,415,644, 3,415,645, 3,415,646 and 3,647,437 are hereby incorporated herein.

In such multicolor applications of diffusion transfer color processes, variations in manufacturing conditions may result in undesired variations in the sensitometric response, e.g., speed, of one silver halide emulsion relative to the sensitometric response of either or both of the other silver halide emulsions. The present invention is concerned with reducing such variations by performing the process in the presence of a reagent effective to improve the sensitometric response of a multicolor photosensitive element.

As noted above, it has been found that processing of a dye developer multicolor photosensitive element in the presence of a pyridine N-oxide substituted in the ortho and/or para position with alkylSO$_2$CH$_2$— effects an increase in speed, and preferentially an increase in the speed of the red-sensitive silver halide emulsion while the speed of the blue-sensitive and green-sensitive emulsions remain relatively constant. The increase in red speed usually is more pronounced at cooler temperatures, i.e., below room temperature.

The subject N-oxides may be initially disposed in the processing composition or in a layer of the element containing the silver halide emulsion(s) or the image-receiving layer, for example, in a layer coated over the photosensitive element or the image-receiving element. Generally, they are incorporated in the processing composition. The N-oxides may be used alone or in combination with each other and are used at a concentration that will give the desired increase in speed, which concentration may be determined empirically. Usually, the N-oxides are employed at a concentration of about 0.1 to 1.0% of the processing composition as initially disposed in the processing composition or subsequently dissolved therein from a layer of the film unit.

This invention will be further illustrated by the following example which is intended to be illustrative only.

EXAMPLE

A multicolor photosensitive element using, as the cyan, magenta and yellow dye developers

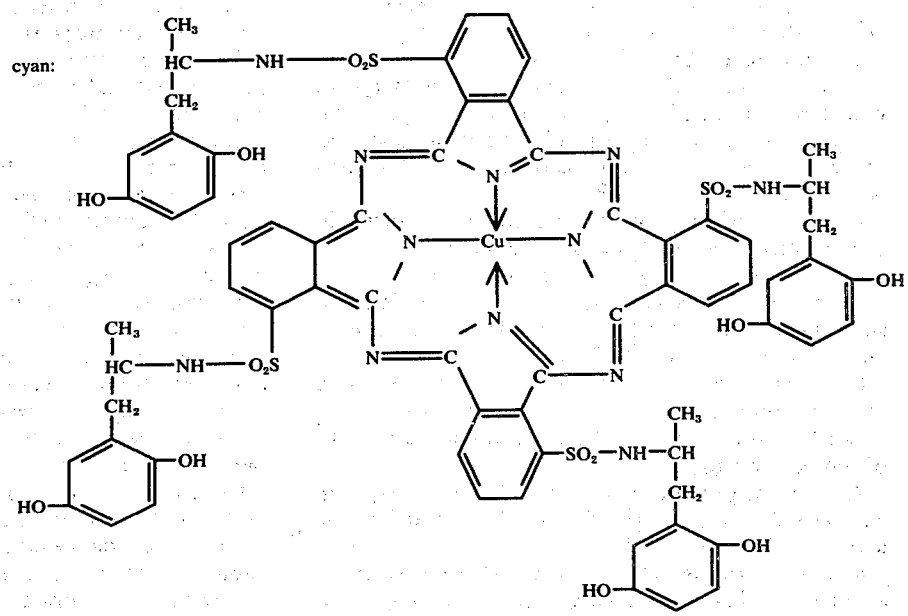

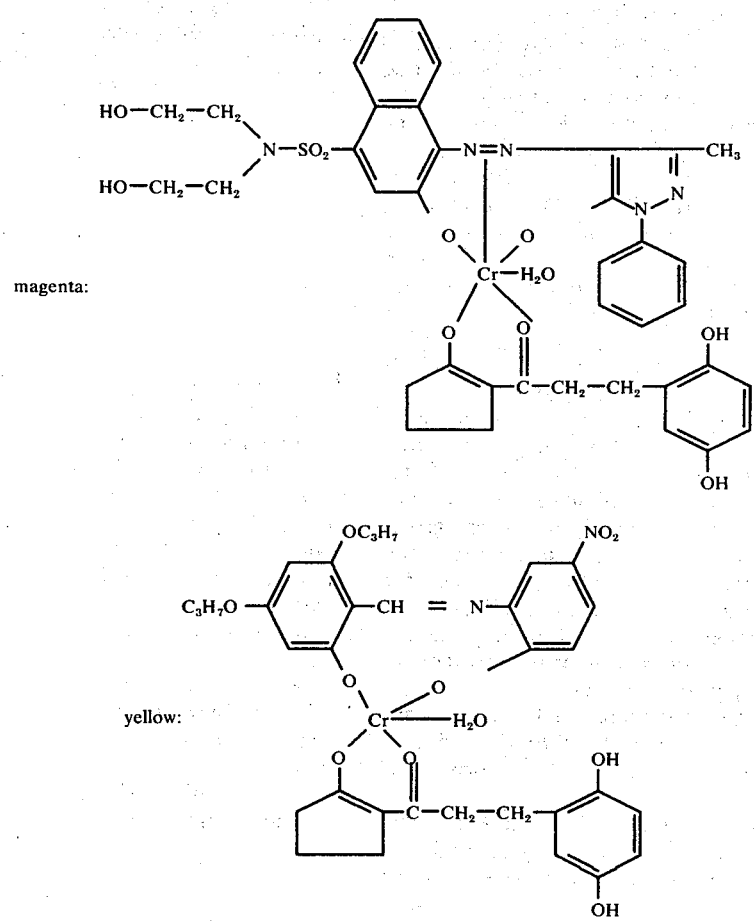

magenta:

yellow:

was prepared by coating a gelatin-subcoated 4 mil opaque polyethylene terephthalate film base with the following layers:

1. a layer of cyan dye developer dispersed in gelatin and coated at a coverage of about 48 mgs./ft.$^2$ of dye and about 98 mgs./ft.$^2$ of gelatin;
2. a red-sensitive gelatino silver iodobromide emulsion coated at a coverage of about 100 mgs./ft.$^2$ of silver and about 125 mgs./ft.$^2$ of gelatin;
3. a layer of a 60-30-4-6 copolymer of butylacrylate, diacetone acrylamide, styrene and methacrylic acid and polyacrylamide coated at a coverage of about 250 mgs./ft$^2$ of the copolymer and about 8 mgs./ft.$^2$ of polyacrylamide;
4. a layer of magenta dye developer dispersed in gelatin and coated at a coverage of about 59 mgs./ft.$^2$ of dye and about 52 mgs./ft.$^2$ of gelatin;
5. a green-sensitive gelatino silver iodobromide emulsion coated at a coverage of about 64 mgs./ft.$^2$ of silver and about 54 mgs./ft.$^2$ of gelatin;
6. a layer containing the copolymer referred to above in layer 3 and polyacrylamide coated at a coverage of about 107 mgs./ft.$^2$ of copolymer and about 12 mgs./ft.$^2$ of polyacrylamide;
7. a layer of yellow dye developer dispersed in gelatin and coated at a coverage of about 80 mgs./ft.$^2$ of dye and about 56 mgs./ft.$^2$ of gelatin;
8. a blue-sensitive gelatino silver iodobromide emulsion layer including the auxiliary developer 4'-methylphenyl hydroquinone coated at a coverage of about 130 mgs./ft.$^2$ of silver, about 60 mgs./ft.$^2$ of gelatin and about 39 mgs./ft.$^2$ of auxiliary developer; and
9. a layer of gelatin coated at a coverage of about 40 mgs./ft.$^2$ of gelatin.

A transparent 4 mil polyethylene terephthalate film base was coated, in succession, with the following layers to form an image-receiving component:

1. as a polymeric acid layer, the partial butyl ester of polyethylene/maleic anhydride copolymer at a coverage of about 2,500 mgs./ft.$^2$;
2. a timing layer containing about a 40:1 ratio of a 60-30-4-6 copolymer of butylacrylate, diacetone acrylamide, styrene and methacrylic acid and polyacrylamide at a coverage of about 500 mgs./ft.$^2$; and
3. a polymeric image-receiving layer containing a 2:1 mixture, by weight, of polyvinyl alcohol and poly-4-vinylpyridine, at a coverage of about 300 mgs./ft.$^2$ The two components thus prepared were then taped together to provide an integral film unit, with a rupturable container retaining an aqueous alkaline processing solution fixedly mounted on the leading edge of each of the components, by pressure-sensitive tapes, so that, upon application of compressive pressure to the container to rupture the container's marginal seal, its contents should be distributed between the image-receiving layer and the gelatin overcoat layer of the photosensitive component. The aqueous alkaline processing composition comprised:

| | | |
|---|---|---|
| Potassium hydroxide (85%) | | 5.4 g. |
| N-benzyl-α-picolinium bromide (50% solution in water) | | 2.50 g. |
| N-phenethyl-α-picolinium bromide (50% solution in water) | | 1.44 g. |
| Sodium carboxymethyl cellulose (Hercules Type 7H4F providing a viscosity of 3,000 cps. at 1% in water at 25° C. 95% solids | | 1.06 g. |
| Titanium dioxide | | 41.8 g. |
| 6-methyl uracil | | 0.29 g. |
| bis-(β-aminoethyl)-sulfide | | 0.02 g. |
| Lithium nitrate | | 0.1 g. |
| Benzotriazole | | 0.56 g. |
| 6-methyl-5-bromo-4-azabenzimidazole | | 0.03 g. |
| Colloidal silica aqueous dispersion (30% SiO$_2$) | | 1.82 g. |
| N-2-hydroxyethyl-N,N',N'-tris-carboxymethyl-ethylene diamine | | 0.83 g. |
| Lithium hydroxide (57.2% solution in water) | | 0.2 g. |
| 6-benzylamino-purine | | 0.39 g. |
| Polyethylene glycol (molecular weight 6,000) | | 0.53 g. |
| | | 2.7 g. |

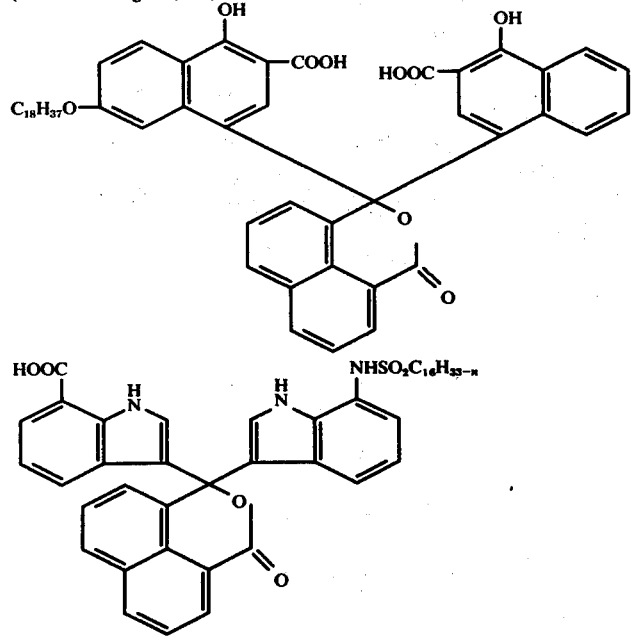

| | 0.6 g. |
|---|---| water to make 100 g.

water to make 100 g.

The photosensitive element was exposed through the transparent support and the layers thereon to a multi-color stepwedge, and a layer approximately 0.0028 inches thick of the processing composition was distributed by passing the film unit between a pair of pressure-applying rolls and into a lighted area. The resulting laminate was maintained intact to provide a multicolor integral negative-positive reflection print.

Using the procedure described above, the alkylsulfonylmethyl-substituted pyridine N-oxides of formulas (1), (3) and (4) were evaluated in the cold (40° F.) at room temperature (70° F.) and in the hot (100° F.). The compounds were added to the aqueous processing composition in the concentration set forth in the Table. As a control the procedure was repeated at the three temperatures omitting the N-oxides.

The .75 speed and the maximum density for red, green and blue were measured for each of the multicolor images obtained at each temperature. The results are set forth in the following Table.

TABLE

| Formula No. % by wt. | | 40° F. Red | 40° F. Green | 40° F. Blue | 70° F. Red | 70° F. Green | 70° F. Blue | 100° F. Red | 100° F. Green | 100° F. Blue |
|---|---|---|---|---|---|---|---|---|---|---|
| (1) | 0.4% | | | | | | | | | |
| | D$_{max}$ | 1.63 | 1.66 | 1.85 | 1.77 | 1.86 | 1.92 | 1.32 | 1.44 | 1.44 |
| | Control | 1.82 | 1.84 | 1.99 | 1.85 | 1.91 | 1.94 | 1.45 | 1.52 | 1.49 |
| | ΔD$_{max}$ | −.19 | −.18 | −.14 | −.08 | −.05 | −.02 | −.13 | −.08 | −.05 |
| | .75 Speed | 1.26 | 1.42 | 1.39 | 1.51 | 1.58 | 1.63 | 1.76 | 1.83 | 1.82 |
| | Control | 0.83 | 1.19 | 1.23 | 1.35 | 1.49 | 1.56 | 1.69 | 1.80 | 1.80 |
| | Δ Speed | 0.43 | 0.23 | 0.16 | 0.16 | 0.09 | 0.07 | 0.07 | 0.03 | 0.02 |
| (3) | 0.5% | | | | | | | | | |
| | D$_{max}$ | 1.78 | 1.86 | 2.00 | 1.74 | 1.80 | 1.85 | 1.27 | 1.37 | 1.37 |

TABLE-continued

| Formula No. % by wt. | | Red | 40° F. Green | Blue | Red | 70° F. Green | Blue | Red | 100° F. Green | Blue |
|---|---|---|---|---|---|---|---|---|---|---|
| | Control | 1.82 | 1.84 | 1.99 | 1.85 | 1.91 | 1.94 | 1.45 | 1.52 | 1.49 |
| | Δ $D_{max}$ | −.04 | 0.02 | 0.01 | −.11 | −.11 | −.09 | −.18 | −.15 | −.12 |
| | .75 Speed | 1.03 | 1.25 | 1.26 | 1.49 | 1.56 | 1.62 | 1.79 | 1.83 | 1.83 |
| | Control | 0.83 | 1.19 | 1.23 | 1.35 | 1.49 | 1.56 | 1.69 | 1.80 | 1.80 |
| | Δ Speed | 0.20 | 0.06 | 0.03 | 0.14 | 0.07 | 0.06 | 0.10 | 0.03 | 0.03 |
| (4) | 0.5% | | | | | | | | | |
| | $D_{max}$ | 1.76 | 1.91 | 1.99 | 1.69 | 1.83 | 1.88 | 1.26 | 1.47 | 1.46 |
| | Control | 1.82 | 1.84 | 1.99 | 1.85 | 1.91 | 1.94 | 1.45 | 1.52 | 1.49 |
| | Δ $D_{max}$ | −.06 | 0.07 | 0.00 | −.16 | −.08 | −.06 | −.19 | −.05 | −.03 |
| | .75 Speed | 1.06 | 1.25 | 1.30 | 1.48 | 1.54 | 1.61 | 1.82 | 1.83 | 1.83 |
| | Control | 0.83 | 1.19 | 1.23 | 1.35 | 1.49 | 1.56 | 1.69 | 1.80 | 1.80 |
| | Δ Speed | 0.23 | 0.06 | 0.07 | 0.13 | 0.05 | 0.05 | 0.13 | 0.03 | 0.03 |

It will be apparent that the relative proportions of the subject compounds and of the other ingredients of the processing composition may be varied to suit the requirements of a given photographic system. Also, it is within the scope of this invention to modify the formulation set forth other than those specifically mentioned. Where desirable, it is also contemplated to include in the processing composition, other components as commonly used in the photographic art.

While the invention has been illustrated as applied to the formation of integral negative-positive multicolor reflection prints, it will be understood that the invention also may be employed in the preparation of other diffusion transfer dye developer images, including monochromatic, black and white, and multicolor transfer images which are separated from the photosensitive layers after image formation. The invention is also applicable to diffusion transfer processes providing integral negative-positive reflection prints wherein the light-reflecting layer is not provided by a pigment in the processing composition but is provided, e.g., by a performed layer of titanium dioxide, and the image-receiving layer is carried by the same support as the photosensitive layers, as taught in U.S. Pat. Nos. 3,594,164 and 3,594,165, both issued July 20, 1971 to Howard G. Rogers.

Since certain changes may be made in the above product and process without departing from the scope of the invention herein involved, it is intended that all matter contained in the above description shall be interpreted as illustrative and not in a limiting sense.

What is claimed is:
1. A compound of the formula

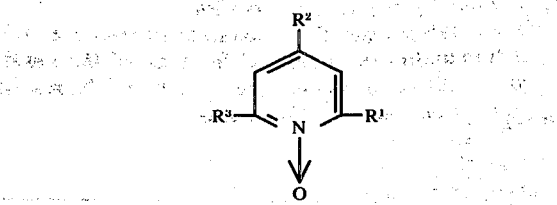

wherein $R^1$ is hydrogen or $-CH_2SO_2R$ wherein R is lower alkyl having 1 to 4 carbon atoms; $R^2$ is hydrogen, lower alkyl having 1 to 4 carbon atoms or said $-CH_2SO_2R$ and $R^3$ is hydrogen or lower alkyl having 1 to 4 carbon atoms, at least one of said $R^1$ and $R^2$ being $-CH_2SO_2R$.

2. A compound as defined in claim 1 wherein $R^1$ is $-CH_2SO_2R$.

3. A compound as defined in claim 1 wherein $R^2$ is $-CH_2SO_2R$.

4. A compound as defined in claim 1 wherein $R^3$ is lower alkyl.

5. A compound as defined in claim 1 wherein said R of said $-CH_2SO_2R$ is methyl.

6. The compound

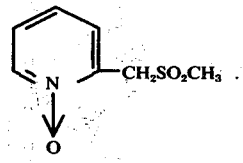

7. The compound

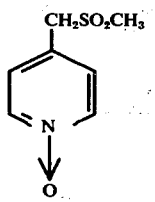

8. The compound

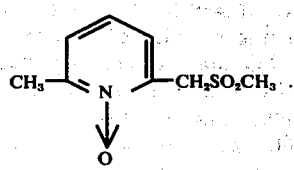

* * * * *